(12) United States Patent
Bellomo et al.

(10) Patent No.: US 11,364,132 B2
(45) Date of Patent: Jun. 21, 2022

(54) DOUBLE WALLED FIXED LENGTH STENT LIKE APPARATUS AND METHODS OF USE THEREOF

(71) Applicant: Restore Medical Ltd., Or Yehuda (IL)

(72) Inventors: Stephen F. Bellomo, Zichron Yakov (IL); Ben Adam Friesem, Tel Aviv (IL); Tanhum Feld, Moshav Merhavia (IL)

(73) Assignee: Restore Medical Ltd., Or Yehuda (IL)

(*) Notice: Subject to any disclaimer, the term of this patent is extended or adjusted under 35 U.S.C. 154(b) by 34 days.

(21) Appl. No.: 16/616,465

(22) PCT Filed: Jun. 4, 2018

(86) PCT No.: PCT/IL2018/050604
§ 371 (c)(1),
(2) Date: Nov. 24, 2019

(87) PCT Pub. No.: WO2018/225059
PCT Pub. Date: Dec. 13, 2018

(65) Prior Publication Data
US 2020/0297516 A1 Sep. 24, 2020

Related U.S. Application Data

(60) Provisional application No. 62/514,984, filed on Jun. 5, 2017.

(51) Int. Cl.
*A61F 2/852* (2013.01)
*A61F 2/915* (2013.01)
*A61F 2/82* (2013.01)

(52) U.S. Cl.
CPC .............. *A61F 2/852* (2013.01); *A61F 2/915* (2013.01); *A61F 2/82* (2013.01); *A61F 2002/91575* (2013.01); *A61F 2250/0063* (2013.01)

(58) Field of Classification Search
CPC .. A61F 2/852; A61F 2/82; A61F 2/915; A61F 2250/0063; A61F 2002/91575
See application file for complete search history.

(56) References Cited

U.S. PATENT DOCUMENTS

| 3,730,186 A | 5/1973 | Edmunds, Jr. et al. |
| 4,183,102 A | 1/1980 | Guiset |

(Continued)

FOREIGN PATENT DOCUMENTS

| CA | 2 970 237 | 6/2016 |
| CN | 1430490 | 7/2003 |

(Continued)

OTHER PUBLICATIONS

International Preliminary Report on Patentability dated Dec. 19, 2019 From the International Bureau of WIPO Re. Application No. PCT/IL2018/050604. (9 Pages).

(Continued)

*Primary Examiner* — Dinah Baria (57) ABSTRACT

A new medical apparatus for deployment within an anatomical blood vessel and methods of use thereof. The apparatus comprising: a first tubular wall; and a second tubular wall, placed within the first tubular wall; wherein the first and second tubular walls are firmly connected at their edges, therefore restricted to have same overall longitudinal length; and wherein the second tubular wall is configured to be partially constricted towards its inner radial axis, while maintaining its overall longitudinal length.

24 Claims, 7 Drawing Sheets

(56) References Cited

U.S. PATENT DOCUMENTS

| | | |
|---|---|---|
| 4,425,908 A | 1/1984 | Simon |
| 4,601,718 A | 7/1986 | Possis et al. |
| 4,950,276 A | 8/1990 | Vince |
| 5,156,620 A | 10/1992 | Pigott |
| 5,167,628 A | 12/1992 | Boyles |
| 5,330,528 A | 7/1994 | Lazim |
| 5,332,403 A | 7/1994 | Kolff |
| 5,383,892 A | 1/1995 | Cardon et al. |
| 5,423,851 A | 6/1995 | Samuels |
| 5,554,180 A | 9/1996 | Turk |
| 5,554,185 A | 9/1996 | Block et al. |
| 5,683,411 A | 11/1997 | Kavteladze et al. |
| 5,755,779 A | 5/1998 | Horiguchi |
| 6,120,534 A | 9/2000 | Ruiz |
| 6,312,462 B1 | 11/2001 | McDermott et al. |
| 6,471,635 B1 | 10/2002 | Forsell |
| 6,533,800 B1 | 3/2003 | Barbut |
| 6,562,066 B1 | 5/2003 | Martin |
| 6,595,980 B1 | 7/2003 | Barbut |
| 6,616,624 B1 | 9/2003 | Kieval |
| 6,638,257 B2 | 10/2003 | Amplatz |
| 6,790,230 B2 | 9/2004 | Beyersdorf et al. |
| 6,936,057 B1 | 8/2005 | Nobles |
| 6,953,476 B1 | 10/2005 | Shalev |
| 7,001,409 B2 | 2/2006 | Amplatz |
| 7,128,750 B1 | 10/2006 | Stergiopulos |
| 7,158,832 B2 | 1/2007 | Kieval et al. |
| 7,201,772 B2 | 4/2007 | Schwammenthal et al. |
| 7,331,993 B2 | 2/2008 | White |
| 7,442,204 B2 | 10/2008 | Schwammenthal et al. |
| 7,497,873 B2 | 3/2009 | Bruckheimer |
| 7,670,367 B1 | 3/2010 | Chouinard et al. |
| 7,862,502 B2 | 1/2011 | Pool et al. |
| 7,935,144 B2 | 5/2011 | Robin et al. |
| 7,983,765 B1 | 7/2011 | Doan et al. |
| 8,070,708 B2 | 12/2011 | Rottenberg et al. |
| 8,091,556 B2 | 1/2012 | Keren et al. |
| 8,597,349 B2 | 12/2013 | Alkhatib |
| 8,663,314 B2 | 3/2014 | Wood et al. |
| 8,696,611 B2 | 4/2014 | Nitzan et al. |
| 8,808,356 B2 | 8/2014 | Braido et al. |
| 8,858,612 B2 | 10/2014 | Ben-Muvhar et al. |
| 8,911,489 B2 | 12/2014 | Ben-Muvhar |
| 8,940,040 B2 | 1/2015 | Shariari |
| 9,034,034 B2 | 5/2015 | Nitzan et al. |
| 9,125,567 B2 | 9/2015 | Gross et al. |
| 9,393,384 B1 | 7/2016 | Kapur et al. |
| 9,474,839 B2 | 10/2016 | Oran et al. |
| 9,532,868 B2 | 1/2017 | Braido |
| 9,572,661 B2 | 2/2017 | Robin et al. |
| 9,603,708 B2 | 3/2017 | Robin et al. |
| 9,629,715 B2 | 4/2017 | Nitzan et al. |
| 9,649,480 B2 | 5/2017 | Sugimoto et al. |
| 9,681,948 B2 | 6/2017 | Levi et al. |
| 9,681,949 B2 | 6/2017 | Braido et al. |
| 9,707,382 B2 | 7/2017 | Nitzan et al. |
| 9,713,696 B2 | 7/2017 | Yacoby et al. |
| 9,724,499 B2 | 8/2017 | Rottenberg et al. |
| 9,744,059 B2 | 8/2017 | Ben-Muvhar |
| 9,775,636 B2 | 10/2017 | Fazio et al. |
| 9,849,006 B2 | 12/2017 | Kozyak et al. |
| 10,568,634 B2 | 2/2020 | Goldie et al. |
| 10,667,931 B2 | 6/2020 | Bruckheimer et al. |
| 2001/0053330 A1 | 12/2001 | Ozaki |
| 2002/0107536 A1 | 8/2002 | Hussein |
| 2003/0032976 A1 | 2/2003 | Boucek |
| 2003/0097172 A1 | 5/2003 | Shalev et al. |
| 2003/0144575 A1 | 7/2003 | Forsell |
| 2003/0149473 A1 | 8/2003 | Chouinard et al. |
| 2003/0167068 A1 | 9/2003 | Amplatz |
| 2003/0236568 A1 | 12/2003 | Hojeibane et al. |
| 2004/0077988 A1 | 4/2004 | Tweden et al. |
| 2004/0111006 A1 | 6/2004 | Alferness et al. |
| 2004/0236412 A1 | 11/2004 | Brar et al. |
| 2005/0096734 A1 | 5/2005 | Majercak et al. |
| 2005/0148925 A1 | 7/2005 | Rottenberg et al. |
| 2005/0165344 A1 | 7/2005 | Dobak, III |
| 2005/0182483 A1 | 8/2005 | Osborne et al. |
| 2005/0234388 A1 | 10/2005 | Amos et al. |
| 2005/0273160 A1 | 12/2005 | Lashinski et al. |
| 2006/0025855 A1 | 2/2006 | Lashinski et al. |
| 2006/0030920 A1 | 2/2006 | Ben-Muvhar |
| 2006/0106449 A1 | 5/2006 | Ben Muvhar |
| 2006/0106450 A1 | 5/2006 | Ben Muvhar |
| 2006/0122692 A1 | 6/2006 | Gilad et al. |
| 2006/0149360 A1 | 7/2006 | Schwammenthal et al. |
| 2006/0178740 A1 | 8/2006 | Stacchino et al. |
| 2006/0241745 A1 | 10/2006 | Solem |
| 2007/0038259 A1 | 2/2007 | Kieval et al. |
| 2007/0043435 A1 | 2/2007 | Seguin et al. |
| 2007/0179590 A1 | 8/2007 | Lu et al. |
| 2007/0198097 A1 | 8/2007 | Zegdi |
| 2007/0213813 A1 | 9/2007 | Von Segesser et al. |
| 2008/0097497 A1 | 4/2008 | Assad et al. |
| 2008/0194905 A1 | 8/2008 | Walsh |
| 2008/0208329 A1 | 8/2008 | Bishop et al. |
| 2009/0099653 A1 | 4/2009 | Suri et al. |
| 2009/0112312 A1 | 4/2009 | LaRose et al. |
| 2009/0149950 A1 | 6/2009 | Wampler |
| 2009/0198315 A1 | 8/2009 | Boudjemline |
| 2009/0270974 A1 | 10/2009 | Berez |
| 2010/0057192 A1 | 3/2010 | Celermajer |
| 2010/0125288 A1 | 5/2010 | Gelfand et al. |
| 2010/0185277 A1 | 7/2010 | Braido et al. |
| 2010/0222633 A1 | 9/2010 | Poirier |
| 2010/0249911 A1 | 9/2010 | Alkhatib |
| 2010/0286758 A1 | 11/2010 | Berglund |
| 2011/0021864 A1 | 1/2011 | Criscione et al. |
| 2011/0046710 A1 | 2/2011 | Mangiardi et al. |
| 2011/0054589 A1 | 3/2011 | Bashir et al. |
| 2011/0071624 A1 | 3/2011 | Finch et al. |
| 2011/0098800 A1 | 4/2011 | Braido et al. |
| 2011/0098802 A1 | 4/2011 | Braido et al. |
| 2011/0213408 A1 | 9/2011 | Gross et al. |
| 2011/0306916 A1 | 12/2011 | Nitzan et al. |
| 2012/0123195 A1 | 5/2012 | Woodruff et al. |
| 2012/0123556 A1 | 5/2012 | Durgin |
| 2012/0165928 A1 | 6/2012 | Nitzan et al. |
| 2012/0310323 A1 | 12/2012 | Roeder |
| 2013/0073026 A1 | 3/2013 | Russo et al. |
| 2013/0096580 A1 | 4/2013 | Cohn et al. |
| 2013/0103162 A1 | 4/2013 | Costello |
| 2013/0172981 A1 | 7/2013 | Gross et al. |
| 2013/0178750 A1 | 7/2013 | Sheehan et al. |
| 2013/0261531 A1 | 10/2013 | Gallagher et al. |
| 2013/0274648 A1 | 10/2013 | Weinberger |
| 2014/0039537 A1 | 2/2014 | Carrison |
| 2014/0128957 A1 | 5/2014 | Losordo et al. |
| 2014/0155997 A1 | 6/2014 | Braido |
| 2014/0277425 A1 | 9/2014 | Dakin |
| 2014/0303710 A1 | 10/2014 | Zhang et al. |
| 2014/0350668 A1 | 11/2014 | Delaloye et al. |
| 2014/0364686 A1 | 12/2014 | McClurg |
| 2015/0073544 A1 | 3/2015 | Gorman, III et al. |
| 2015/0148896 A1 | 5/2015 | Karapetian et al. |
| 2015/0174308 A1 | 6/2015 | Oran et al. |
| 2016/0151153 A1 | 6/2016 | Sandstrom et al. |
| 2017/0042551 A1 | 2/2017 | Celermajer et al. |
| 2017/0065402 A1 | 3/2017 | Tozzi et al. |
| 2017/0172771 A1 | 6/2017 | Bruckjeimer et al. |
| 2017/0215885 A1 | 8/2017 | Goldie et al. |
| 2017/0216025 A1 | 8/2017 | Nitzan et al. |
| 2017/0325946 A1 | 11/2017 | Bell et al. |
| 2017/0340441 A1 | 11/2017 | Rowe |
| 2017/0340460 A1 | 11/2017 | Rosen et al. |
| 2017/0367855 A1 | 12/2017 | Jenni |
| 2018/0021156 A1 | 1/2018 | Ben-Muvhar et al. |
| 2018/0036109 A1 | 2/2018 | Karavany et al. |
| 2018/0085128 A1 | 3/2018 | Belllomo et al. |
| 2020/0000582 A1 | 1/2020 | Lashinski et al. |
| 2020/0289299 A1 | 9/2020 | Bruckheimer et al. |

(56) References Cited

U.S. PATENT DOCUMENTS

| | | |
|---|---|---|
| 2020/0360024 A1 | 11/2020 | Bellomo et al. |
| 2021/0338465 A1 | 11/2021 | Bruckheimer et al. |

FOREIGN PATENT DOCUMENTS

| | | |
|---|---|---|
| CN | 1672644 | 9/2005 |
| CN | 101687088 | 3/2010 |
| CN | 102764170 | 11/2012 |
| CN | 102961200 | 3/2013 |
| CN | 103202735 | 7/2013 |
| CN | 103930042 | 7/2014 |
| CN | 204106100 | 1/2015 |
| CN | 105392431 | 3/2016 |
| DE | 10102045 | 1/2003 |
| EP | 1576929 | 9/2005 |
| EP | 1849440 | 10/2007 |
| EP | 1870057 | 12/2007 |
| EP | 2567663 | 3/2013 |
| EP | 3300672 | 4/2018 |
| WO | WO 2001/035861 | 5/2001 |
| WO | WO 03/028522 | 4/2003 |
| WO | WO2003/028522 | 4/2003 |
| WO | WO 2005/084730 | 9/2005 |
| WO | WO 2006/131930 | 12/2006 |
| WO | WO2007/129220 | 11/2007 |
| WO | WO2007/144782 | 12/2007 |
| WO | WO 2011/156176 | 12/2011 |
| WO | WO 2016/013006 | 1/2016 |
| WO | WO 2016/096529 | 6/2016 |
| WO | WO2016/096529 | 6/2016 |
| WO | WO 2017/024357 | 2/2017 |
| WO | WO 2017/194437 | 11/2017 |
| WO | WO 2018/225059 | 12/2018 |

OTHER PUBLICATIONS

International Search Report and the Written Opinion dated Sep. 20, 2018 From the International Searching Authority Re. Application No. PCT/IL2018/050604. (12 Pages).
Supplementary European Search Report and the European Search Opinion dated Feb. 4, 2021 From the European Patent Office Re. Application No. 18812772.4. (7 Pages).
Communication Pursuant to Article 94(3) EPC dated Jan. 3, 2020 From the European Patent Office Re. Application No. 17193799.8. (4 Pages).
European Search Report and the European Search Opinion dated Jan. 19, 2018 From the European Patent Office Re. Application No. 17193799.8. (9 Pages).
Final Official Action dated Jul. 2, 2020 from the US Patent and Trademark Office Re. U.S. Appl. No. 15/716,667. (16 pages).
International Preliminary Report on Patentability dated Jan. 24, 2017 From the International Bureau of WIPO Re. Application No. PCT/IL2015/050745. (8 Pages).
International Search Report and the Written Opinion dated Nov. 5, 2015 From the International Searching Authority Re. Application No. PCT/IL2015/050745. (14 Pages).
Notice of Allowance dated Jan. 24, 2020 From the US Patent and Trademark Office Re. U.S. Appl. No. 15/327,075. (8 pages).
Notification of Office Action and Search Report dated Nov. 30, 2021 From the State Intellectual Property Office of the People's Republic of China Re. Application No. 201710896715.3 together with an English Summary (12 Pages).
Office Action dated Jun. 7, 2021 From the Israel Patent Office Re. Application No. 250181 and Its Translation Into English. (7 Pages).
Office Action dated May 12, 2020 From the Israel Patent Office Re. Application No. 250181 and Its Translation Into English. (7 Pages).
Office Action dated Oct. 19, 2020 From the Israel Patent Office Re. Application No. 254791 and Its Translation Into English. (6 Pages).
Official Action dated Feb. 2, 2018 From the US Patent and Trademark Office Re. U.S. Appl. No. 15/327,075. (15 pages).

Official Action dated Dec. 3, 2019 From the US Patent and Trademark Office Re. U.S. Appl. No. 15/716,667. (18 pages).
Official Action dated Jun. 5, 2019 From the US Patent and Trademark Office Re. U.S. Appl. No. 15/327,075. (6 Pages).
Official Action dated Sep. 6, 2018 From the US Patent and Trademark Office Re. U.S. Appl. No. 15/327,075. (9 pages).
Official Action dated Aug. 13, 2021 from the US Patent and Trademark Office Re. U.S. Appl. No. 15/716,667. (19 pages).
Official Action dated Dec. 20, 2018 From the US Patent and Trademark Office Re. U.S. Appl. No. 15/327,075. (12 pages).
Official Action dated Sep. 27, 2019 From the US Patent and Trademark Office Re. U.S. Appl. No. 15/327,075. (6 Pages).
Supplementary European Search Report and the European Search Opinion dated Feb. 9, 2018 From the European Patent Office Re. Application No. 15825239.5. (7 Pages).
Ahmadi et al. "Percutaneously Adjustable Pulmonary Artery Band", The Annals of the Thoracic Surgery, 60(6/Suppl.): S520-S522, Dec. 1995.
Amahzoune et al. "A New Endovascular Size Reducer for Large Pulmonary Outflow Tract", European Journal of Cardio-Thoracic Surgery, 37(3): 730-752, Available Online Oct. 2, 2009.
Bailey "Back to the Future! Bold New Indication for Pulmonary Artery Banding", The Journal of Heart and Lung Transplantation, 32(5): 482-483, May 1, 2013.
Basquin et al. "Transcatheter Valve Insertion in a Model of Enlarged Right Ventricular Outflow Tracts", The Journal of Thoracic and Cardiovascular Surgery, 139(1): 198-208, Jan. 2010.
Boudjemline et al. "Percutaneous Pulmonary Valve Replacement in a Large Right Ventricular Outflow Tract. An Experimental Study", Journal of the American College of Cardiology, 43(6): 1082-1087, Mar. 17, 2004.
Boudjemline et al. "Steps Toward the Peercutaneous Replacement of Atrioventricular Valves. An Experimental Study", Journal of the American College of Cardiology, 46(2): 360-365, Jul. 19, 2005.
Corno et al. "The Non-Circular Shape of FloWatch®-PAB Prvents the Need for Pulmonary Artery Reconstruction After Banding. Computational Fluid Dynamics and Clinical Correlations", European Journal of Cardio-Thoracic Surgery, 29(1): 93-99, Available Online Dec. 6, 2005.
DiBardino et al. "A Method of Transcutaneously Adjustable Pulmonary Artery Banding for Staged Left Ventricular Retraining", The Journal of Thoracic and Cardiovascular Surgery, 144(3): 553-556, Published Online Feb. 9, 2012.
Horita et al. "Development of a Reexpandable Covered Stent for Children", Catheterization and Cardiovascular Interventions. 68(5): 727-734, Published Online Oct. 12, 2006.
Le Bret el al. "A New Percutaneously Adjustable, Thoracoscopically Implantable, Pulmonary Artery Banding: An Experimental Study", The Annals of Thoracic Surgery, 72(4): 1358-1361, Oct. 31, 2001.
Mollet et al. "Development of a Device for Transcatheter Pulmonary Artery Banding: Evaluation in Animals", European Heart Journal, 27(24): 3065-3072, Published Ahead of Print Oct. 31, 2006.
Mollet et al. "Off-Pump Replacement of the Pulmonary Valve in Large Right Ventricular Outflow Tracts: A Transcathcter Approach Using an Intravascular Infundibulum Reducer", Pediatric Research, 62(4): 428-433, Oct. 2007.
Nakahata et al. "Percutaneous Bilateral Pulmonary Artery Banding Using a Re-Expandable Covered Stent: Preliminary Animal Study", The Kisato Medical Journal, 41(2): 165-169, Sep. 2011.
Schranz et al. "Pulmonary Artery Banding in Infants and Young Children With Left Ventricular Dilated Cardiomyopathy: A Novel Therapeutic Strategy Before Heart Transplantation", The Journal of Heart and Lung Transplantation, 32(5): 475-481, Published Online Feb. 12, 2013.
Schranz et al. "Pulmonary Artery Banding in Infants and Young Children With Lleft Ventricular Dilated Cardiomyopathy: A Novel Therapeutic Strategy Before Heart Transplantation", The Journal of Heart and Lung Transplantation, 32(5):475-481, May 31, 2013.
Talwar et al. "Changing Outcomes of Pulmonary Artery Banding With the Percutaneoulsy Adjustable Pulmonary Artery Band", The Annals of Thoracic Surgery, 85(2): 593-598, Feb. 2008.

(56) References Cited

OTHER PUBLICATIONS

Watanabe et al. "How to Clamp the Main Pulmonary Artery During Video-Assisted Thorascopic Surgery Lobectomy", European Journal of Cardio-Thoracic Surgery, 31(1): 129-131, Published Online Nov. 29, 2006.
Final Official Action dated Feb. 22, 2022 from US Patent and Trademark Office Re. U.S. Appl. No. 15/716,667. (23 pages).
English Summary dated Mar. 17, 2022 of Notification of Office Action and Search Report dated Mar. 9, 2022 From the State Intellectual Property Office of the People's Republic of China Re. Application No. 201880036104.4. (2 Pages).
Interview Summary dated Apr. 13, 2022 from U.S. Patent and Trademark Office Re. U.S. Appl. No. 15/716,667. (2 pages).
Notification of Office Action and Search Report dated Mar. 9, 2022 From the State Intellectual Property Office of the People's Republic of China Re. Application No. 201880036104.4. (8 Pages).

Distal Side                                              Proximal side

DOUBLE WALLED FIXED LENGTH STENT LIKE APPARATUS AND METHODS OF USE THEREOF

RELATED APPLICATIONS

This application is a National Phase of PCT Patent Application No. PCT/IL2018/050604 having International filing date of Jun. 4, 2018, which claims the benefit of priority under 35 USC § 119(e) of U.S. Provisional Patent Application No. 62/514,984 filed on Jun. 5, 2017. The contents of the above applications are all incorporated by reference as if fully set forth herein in their entirety.

FIELD OF THE INVENTION

The current invention relates to a medical device to be positioned within the main pulmonary artery and/or the pulmonary artery branches, and to methods of use thereof for treating, reducing the severity of, or reducing symptoms associated with, or any combination thereof, congestive heart failure, including left ventricular failure, wherein use may in certain embodiments, affect the position and function of the interventricular septum during systole.

BACKGROUND OF THE INVENTION

Congestive heart failure (CHF) is a condition in which the heart does not pump out sufficient blood to meet the body's demands. CHF can result from either a reduced ability of the heart muscle to contract (systolic failure) or from a mechanical problem that limits the ability of the heart's chambers to fill with blood (diastolic failure). When weakened, the heart is unable to keep up with the demands placed upon it and the left ventricle (LV) may get backed up or congested. CHF is a progressive disease. Failure of the left side of the heart (left-heart failure/left-sided failure/left-ventricle failure) is the most common form of the disease.

CHF affects people of all ages including children, but it occurs most frequently in those over age 60, and is the leading cause of hospitalization and death in that age group. Current treatments of CHF include lifestyle changes, medications, and surgery to bypass blocked blood vessels, replace regurgitant or stenotic valves, install stents to open narrowed coronary vessels, install pump assist devices or transplantation of the heart.

Normal cardiac contraction is a finely tuned orchestrated activity dependent on muscle function, ventricular geometry and loading conditions termed preload and afterload. When CHF due to LV systolic failure occurs it is typically associated with changes in the geometry of the ventricles, often called remodeling. The LV becomes dilated and the interventricular septum is deflected into the right ventricle (RV), resulting in decreased LV output/pumping efficiency. The efficient systolic function of the LV is dependent not only on the strength of the myocardium but also on the LV geometry, the position and shape of the interventricular septum and the geometry and function of the RV. Interventricular dependence has been documented in experimental studies which have evaluated both normal and pathological preparations in animals. LV systolic function can be directly influenced by interventions affecting the RV and the position of the interventricular septum.

Surgical pulmonary artery banding (PAB) is a technique that was described more than 60 years ago and is still in use today for children and infants with congenital heart defects, such as overflow of blood to the lungs and volume overload of the RV. PAB is typically performed through a thoracotomy and involves wrapping a band around the exterior of the main pulmonary artery (MPA) and fixing the band in place, often with the use of sutures. Once applied, the band is tightened, narrowing the diameter of the MPA, increasing resistance to flow, reducing blood flow to the lungs, and reducing downstream pulmonary artery (PA) pressure.

Surgical PAB procedures involve the risks present with all surgical procedures. In addition, use of surgical PAB has a number of particular disadvantages and drawbacks. Primary among these drawbacks is the inability of the surgeon performing the procedure to accurately assess, from the hemodynamic standpoint, the optimal final diameter to which the PA should be adjusted. Often, the surgeon must rely upon his or her experience in adjusting the band to achieve acceptable forward flow while decreasing the blood flow sufficiently to protect the pulmonary vasculature.

It is also not uncommon for the band to migrate towards one of the pulmonary artery branches (usually the left), resulting in stenosis of the other pulmonary artery branch (usually the right). There have also been reports of hardening of the vessels around the band due to buildup of calcium deposits and scarring of the PA wall beneath the band, which can also inhibit blood flow. Flow resistance due to PAB may change over time, and additional surgeries to adjust band tightness occur in up to one third of patients. The band is typically removed in a subsequent operation, for example, when a congenital malformation is corrected in the child or infant.

In addition to the classical use of PAB for treatment of congenital defects in infants and children, there has been a recent report of use of surgical PAB for left ventricle dilated cardiomyopathy (LVDCM) in infants and young children. This method includes increasing the pressure load on the right ventricle by surgically placing a band around the pulmonary artery. The increased pressure in the right ventricle caused a leftward shift of the interventricular septum and improvement of left ventricle function. It was found that the optimal degree of constriction was achieved when the RV pressure was approximately 60% to 70% of the systemic level and so that the interventricular septum slightly moved to a midline position. The success of these procedures in infants and children has been reported to be possibly due to the potential for myocyte recovery and repopulation being significantly greater for infants and young children than for adults. However, it is the position of the inventors that the geometric improvements to the failing heart due to PAB may be responsible, at least partially, for the observed improvements in LV function, and therefore PAB for adult left ventricle heart failure may demonstrate similar improvement in LV function.

The MPA is not a favorable location for positioning an implant due to its relatively large diameter (~30 mm) and short length (~50 mm). The full length of the MPA is not usable for an implant due to the proximity to the pulmonary valve on one end, and the bifurcation to the pulmonary branches on the other. It is estimated that the usable length of the MPA for the implant is approximately 30 mm. Implantation of a short, wide device into the MPA is very difficult, and there is significant danger that the device will rotate or otherwise not be placed concentric with the MPA, in which case near complete blockage of the MPA could occur. In addition, the device may erroneously be placed either too close to the pulmonary valve or to the bifurcation. The branch pulmonary arteries are more favorable for placement of an implant due to their smaller diameter than the MPA and the longer available length for placement of an implant. When implants are placed in the branch PAs, it is required to place two implants in a bilateral fashion, in order to cause an increase in RV pressure.

Accordingly, there is a need to provide a relatively simple medical apparatus, which could be implanted in a minimally-invasive fashion, and which can allow an adjustment of blood flow through a vessel. There is also a need for gradual reduction in the diameter of the MPA or branch PAs, which is not currently feasible with the surgical PAB approaches described above. In addition, there is a need to use the medical apparatus for treatment of the mature adult population suffering from left ventricle (LV) failure.

SUMMARY OF THE INVENTION

The methods and apparatuses of the invention describe a medical apparatus configured to reduce a diameter of a blood vessel for treating or at least reducing the severity of a congestive failure of the heart, such as but not limited to: systolic heart failure, diastolic heart failure, left ventricle (LV) heart failure, right ventricle (RV) heart failure, congenital defects of the heart for which surgical pulmonary artery banding (PAB) is used, and any other condition which requires pulmonary artery banding (PAB).

Some embodiments of the present invention provide a new medical apparatus for deployment within an anatomical blood vessel comprising:
a first tubular wall; and
a second tubular wall, placed within the first tubular wall;
wherein the first and second tubular walls are firmly connected at their edges, therefore restricted to have same overall longitudinal length (L); and
wherein the second tubular wall is configured to be partially constricted towards its inner radial axis, while maintaining its overall longitudinal length;
accordingly, the combination of the first and second tubular walls forms a diametrical reducer.

In some embodiments, the second tubular wall comprises plurality of section elements, wherein at least some of the sections elements are configured to allow a motion of at least some of the section elements one relative to another, when a constriction force is applied.

In some embodiments, at least some of the section elements are configured to be deformed, when a constriction force is applied.

In some embodiments, the plurality of section elements comprise strut elements and connecting elements; and wherein the connecting elements are configured to be deformed, when a constriction force is applied.

In some embodiments, at least some of the section elements are arranged in rows or rings-like configuration.

In some embodiments, the section elements' motion comprises at least one of: deformation, translation, rotation, twist, contraction, conversion and collapse.

In some embodiments, at least one of the first- and the second-tubular walls comprises binding elements at its edges, configured for the connection of the first and the second tubular walls one to another.

In some embodiments, the apparatus further comprising a constricting element configured to constrict a circumference of a portion of the second tubular wall.

In some embodiments, the constriction provides the second tubular wall with a radial neck section, configured for reduction of the effective diameter of the anatomical blood vessel.

In some embodiments, at least a portion of the second tubular wall is coated with a coating material.

In some embodiments, the constriction is provided, while the medical apparatus is within the anatomic vessel.

In some embodiments, the first and second tubular walls are concentric.

In some embodiments, material of the first and second tubular walls comprises at least one of the group consisting of: Nitinol, stainless steel, Titanium, Cobalt-Chromium alloy, Tantalum alloy, polymer, Platinum alloy and any combination thereof.

In some embodiments, the first tubular wall is made of a first material and the second tubular wall is made of a second material.

In some embodiments, the first and second tubular walls are manufactured by a laser cut process.

In some embodiments, the ratio between the medical apparatus's longitudinal length and diameter of the first tubular wall is smaller than three (3).

In some embodiments, the medical apparatus is reversibly collapsible and configured to be delivered into the anatomic vessel via a catheter.

Some embodiments of the present invention provide a new method of use of an apparatus configured for reduction of effective diameter of an anatomic vessel, the method comprising:
providing a medical apparatus having a second tubular wall placed within a first tubular wall;
deploying the medical apparatus within an anatomical blood vessel; and
constricting at least a portion of the second tubular wall, thereby providing the second tubular wall with a radial neck section, while maintaining its overall longitudinal length.

In some embodiments, the step of providing comprises partially constricting the second tubular wall.

In some embodiments, the step of providing comprises at least partially coating the second tubular wall.

In some embodiments, the step of providing comprises connecting both the first- and the second-tubular walls at their edges, thereby restricting the first- and the second-tubular walls to have the same overall longitudinal length.

In some embodiments, the step of deploying comprises delivering the medical apparatus into an anatomical blood vessel via a catheter.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may be understood by reference to the following detailed description when read with the accompanying drawings in which:

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

The following description is provided, alongside all chapters of the present invention, so that to enable any person skilled in the art to make use of the invention and sets forth the best modes contemplated by the inventor of carrying out this invention. Various modifications, however, will remain apparent to those skilled in the art, since the generic principles of the present invention have been defined specifically to provide a medical apparatus configured to reduce a diameter of a blood vessel for treating or at least reducing the severity of a congestive failure of the heart, such as but not limited to: systolic heart failure, diastolic heart failure, left ventricle (LV) heart failure, right ventricle (RV) heart failure, congenital defects of the heart for which surgical pulmonary artery banding (PAB) is used, and any other condition which requires pulmonary artery banding (PAB).

As used herein, in one embodiment, the term "about", refers to a deviance of between 0.0001-5% from the indicated number or range of numbers. In one embodiment, the term "about", refers to a deviance of between 1-10% from the indicated number or range of numbers. In one embodiment, the term "about", refers to a deviance of up to 25% from the indicated number or range of numbers.

According to some embodiments, the term "a" or "one" or "an" refers to at least one.

Figure 1:
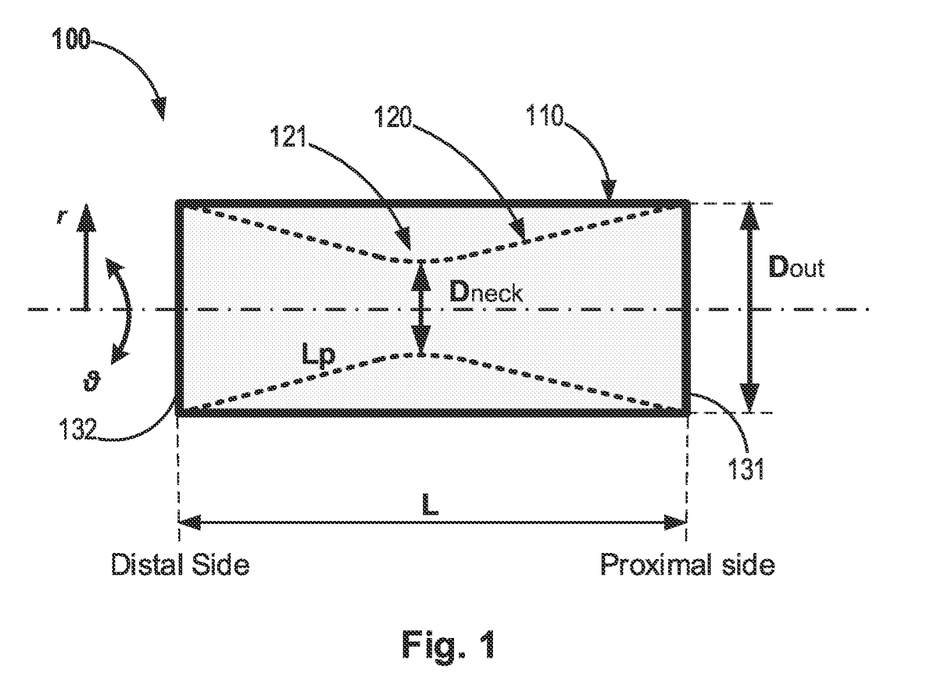
FIG. 1 conceptually depicts a stent like medical apparatus having first and second tubular walls, according to some embodiments of the invention.

According to some embodiments the present invention provides a stent like medical apparatus for deployment within an anatomical blood vessel, as demonstrated at least in FIG. 1, which is configured to reduce the effective diameter of an anatomical blood vessel.

According to some embodiments, the medical apparatus 100 comprises:
  a first tubular wall 110 (also noted as outer tubular wall); and
  a second tubular wall 120 (also noted as inner tubular wall), placed within the first tubular wall;
  wherein the first- and second-tubular walls are firmly connected (one to another) at their proximal- and distal-edges 131,132, therefore restricted to have same overall longitudinal length (L); and wherein the second tubular wall is configured to be partially constricted 121 towards its inner radial axis, while maintaining its overall longitudinal length; it is therefore that the combination of the first and second tubular walls forms a diametrical reducer.

According to some embodiments, the constriction process may be applied after the deployment of the apparatus within an anatomical blood vessel.

According to some embodiments, the constriction is provided while the medical apparatus is within the anatomic vessel. According to some embodiments, the constriction provides the second tubular wall with a radial neck section, configured for reduction of the effective diameter of the anatomical blood vessel. According to some embodiments, at least a portion of the second tubular wall is coated with a coating material, as further demonstrated in FIG. 7, 760.

Figure 7:
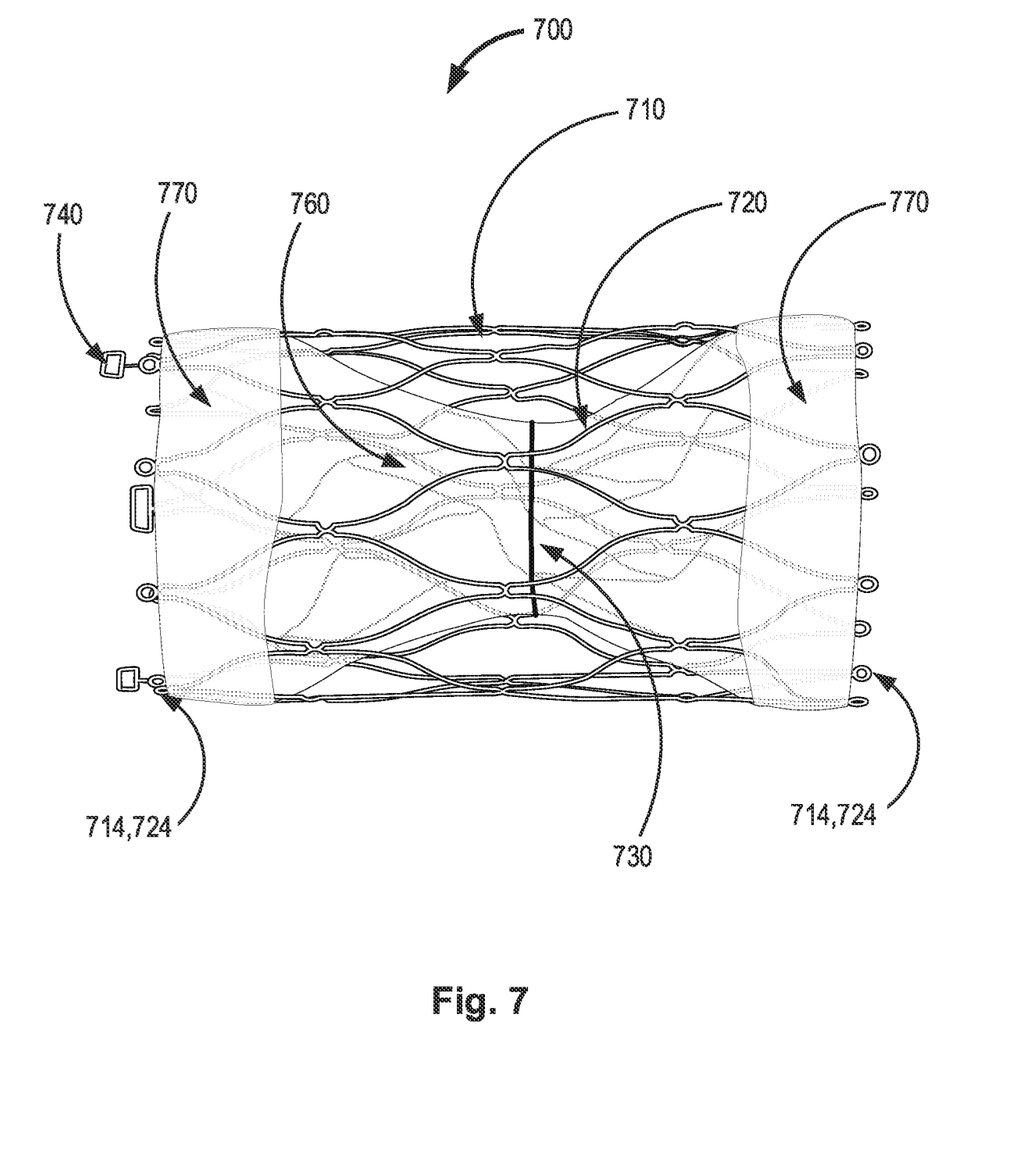
FIG. 7 conceptually depicts a stent like medical apparatus having a first tubular wall and a second coated tubular wall, according to some embodiments of the invention.

According to some embodiments, in addition to the coating of the second tubular wall, two bands of coating on the proximal and distal ends of the first tubular wall can be applied, configured to create a fluid seal with the coating of the second tubular wall, as further demonstrated in FIG. 7, 770.

The coating material can be selected, for a non-limiting example, from: silicone elastomers, urethane containing polymers (such as polyurethane, silicone-polyurethane, polycarbonate urethanes, and silicone polycarbonate urethanes), PTFE (polytetrafluoroethylene), ePTFE (expanded PTFE), PLA (including PLGA, PLLA), xenograft or allograft tissue (such as pericardial tissue).

According to some embodiments, the second tubular wall comprises a plurality of section elements, wherein at least some of the section elements are configured to allow a motion of at least some of the section elements one relative to another, when a constriction force is applied.

Figure 2A:
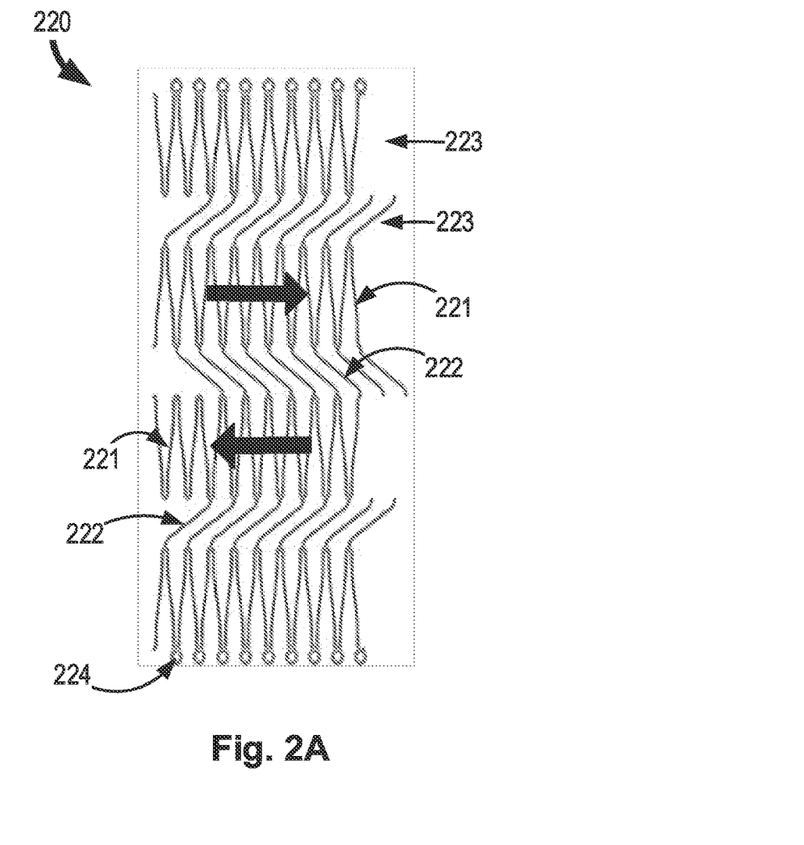
FIGS. 2A and 2B conceptually depict a flattened image and picture image of a second tubular wall, respectively, according to some embodiments of the invention.
Figure 2B:
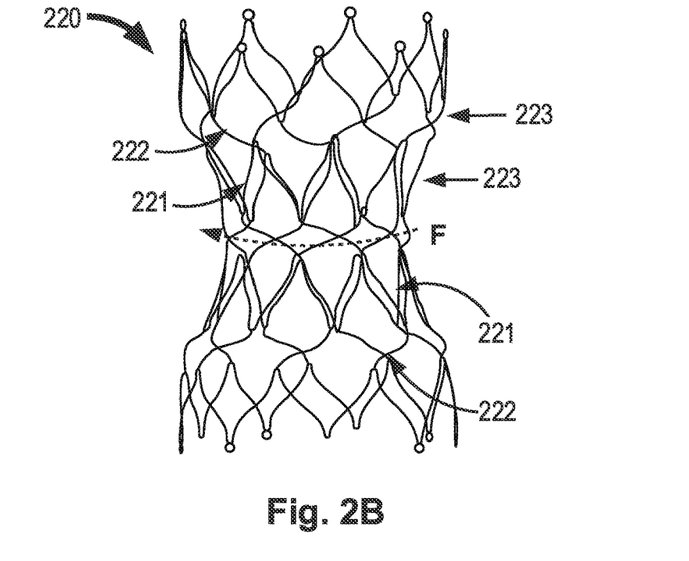

Reference is now made to FIGS. 2A and 2B, which schematically demonstrate a second tubular wall, according to some embodiments of the invention. FIG. 2A illustrates a flattened second tubular wall, shown after the process of laser cutting, according to some embodiments of the invention. FIG. 2B depicts a picture of a second tubular wall after constriction due to a constriction force (F), according to some embodiments of the invention.

As shown in both FIGS. 2A and 2B the second tubular wall 220 comprises, according to some embodiments, a plurality of connected section elements 221, 222, wherein at least some of the section elements are configured to be deformed when a force, for example a constriction force (F), is applied thereon. The deformed section elements allow a motion of some of the section elements one relative to another, therefore configured to allow a constriction of at least a part of the second tabular wall. Consequently, the deformed section elements allow the second tubular wall to expand its path length (Lp), during the radial constriction, while maintaining its overall longitudinal length (L).

According to some embodiments the plurality of section elements can all have a similar shape and/or configuration. According to other embodiments the plurality of section elements can have a variety of shapes and/or configurations.

According to some embodiments, the plurality of section elements can comprise strut elements 221 and connecting elements 222, as demonstrated in FIGS. 2A and 2B. The connecting elements are configured to be deformed when a constriction force (F) is applied, and thereby configured to allow an increase in the distance between the strut elements rows/rings. The deformation of the connecting elements consequently allows the constriction of at least a part of the second tubular wall, with an increased path length (Lp), while maintaining its overall longitudinal length (L). According to some embodiments, the strut elements 222 can also be deformed by the constricting force, however in a much smaller deformation extent than of the connecting elements.

In the examples of FIGS. 2A and 2B, the increased distance between the strut elements is enabled by twisting of rows/rings of strut elements, one relative to the other via the connecting elements, as demonstrated by the marked arrows in the flattened schematic illustration in FIG. 2A. In other embodiments, and as demonstrated in FIGS. 6C and 6D, the increased distance between the strut elements is enabled by extension of the connecting elements 622,632.

According to some embodiments, at least some of the section elements are arranged in rows or rings-like configuration 223. The rings 223 are configured to move one relative to another, during the constriction.

According to some embodiments, the motion of the section elements comprises at least one of: translation, deformation, rotation, twist, contraction, conversion and collapse.

Figure 3:
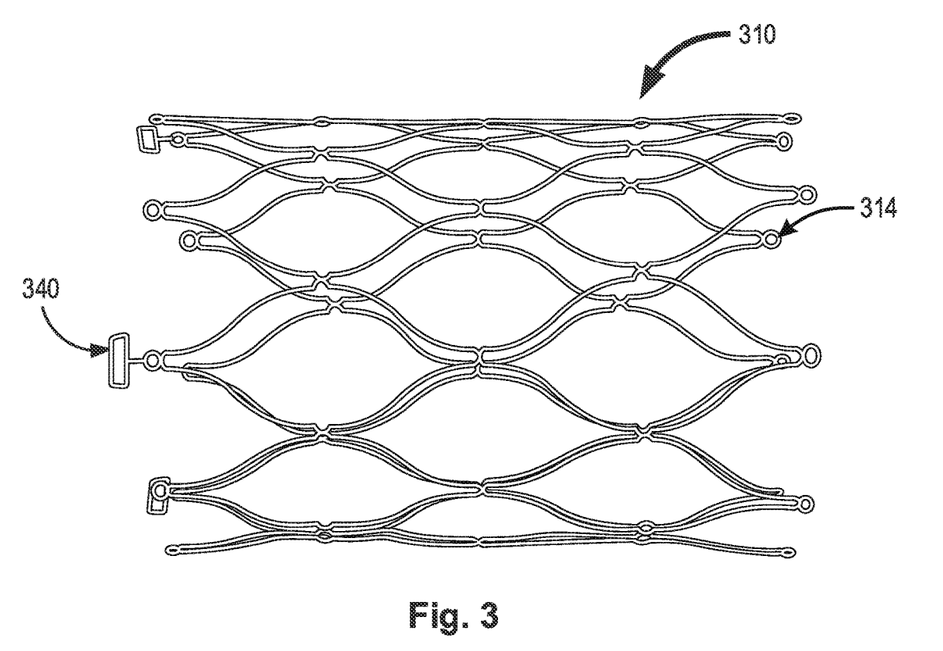
FIG. 3 conceptually depicts a first tubular wall, according to some embodiments of the invention.

According to some embodiments, at least one of the first and the second tubular walls comprises binding elements 224,314 at its edges, configured for the connection of the first and the second tubular walls one to another. According to some embodiments, the connection can be by a suture, adhesion, welding, mechanical connection, or any other means of connection.

Reference is now made to FIG. 3, which demonstrates a first tubular wall, according to some embodiments of the invention. The first tubular wall 310 as demonstrated comprises binding elements 314 at its edges, configured for the connection of the first and the second tubular walls one to another. According to some embodiments the first tubular wall further comprises at least one grip element 340 (and 740, FIG. 7), at least at one edge thereof. The grip element is configured to be pulled and thereby assist in loading the medical apparatus, for its insertion into a delivery system, as further demonstrated in FIG. 5A, and/or for re-sheathing of the apparatus into the delivery system during the process of deployment into the target vessel.

Figure 4:
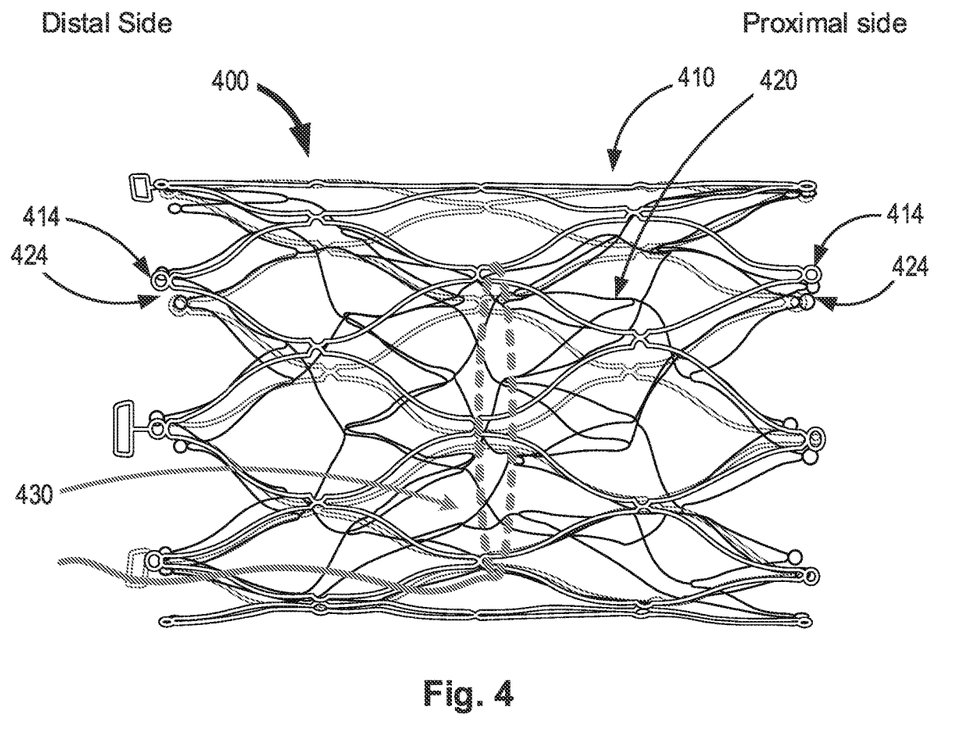
FIG. 4 conceptually depicts a stent like medical apparatus, in a constricted configuration, according to some embodiments of the invention.

Reference is now made to FIG. 4, which demonstrates a medical apparatus 400 comprising the first tubular wall 410 and the second tubular wall 420 bound together at both their proximal and distal ends via their binding elements 414,424, and where the medical apparatus is shown in a partially constricted configuration. According to some embodiments, the apparatus further comprises a constricting element 430 configured to constrict a circumference of a portion of the second tubular wall 420.

According to some embodiments the constriction of the second tubular wall can be provided before- and/or after- the deployment of the apparatus within the vessel; therefore, can be provided with an initial constricted state and/or constricted in real time to a final constricted state, respectively.

Figure 5A:
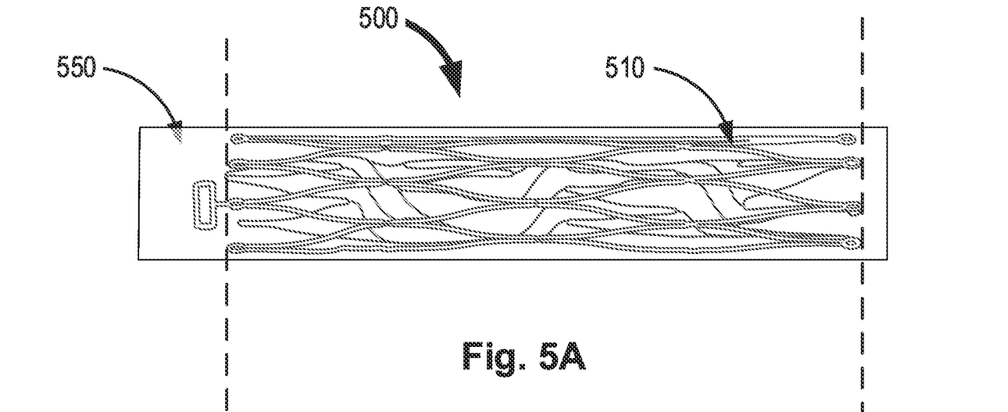
FIG. 5A conceptually depicts a medical apparatus crimped within a delivery system, according to some embodiments of the invention.
Figure 5B:
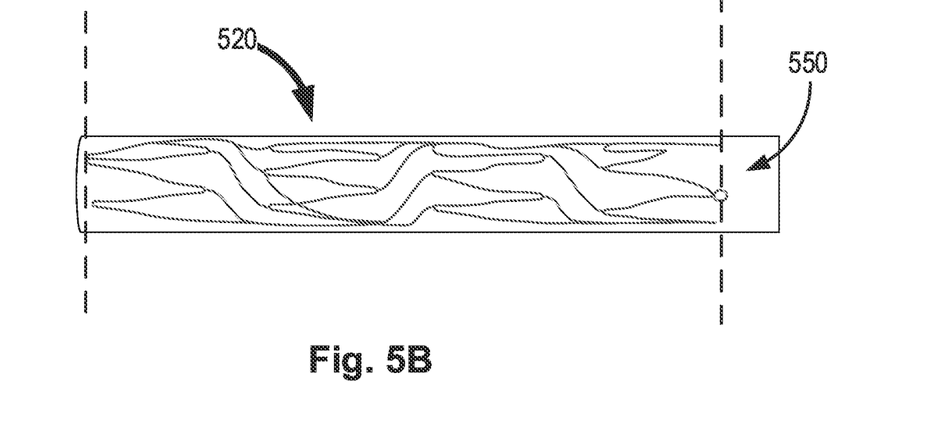
FIG. 5B conceptually illustrates a crimped second tubular wall, according to some embodiments of the invention.

Reference is now made to FIGS. 5A and 5B, which demonstrate a stent-like medical apparatus 500, according to some embodiments of the invention. As demonstrated the stent-like medical apparatus is configured for a reversible collapse and therefore configured to be delivered into the anatomic vessel via a catheter tube. FIG. 5A demonstrates the collapsed/crimped apparatus 500 within the delivery catheter 550, whereas FIG. 5B demonstrates only the collapsed second tubular wall 520, within the delivery catheter 550, which is hidden by the first tubular wall at FIG. 5A. According to some embodiments, the overall longitudinal length (Lc) of the collapsed/crimped apparatus is larger than the overall longitudinal length (L) of the non-collapsed apparatus, (Lc>L).

According to some embodiments, the overall longitudinal lengths of first and second tubular walls are the same whether in a crimped configuration (in a delivery catheter), a deployed configuration (in a vessel), or a constricted configuration (having an hourglass shape).

According to some embodiments, at least one of the outer and inner tubular walls is made of a collapsible memory shape material, therefore self-expanding material. According to some embodiments, at least one of the outer and inner tubular walls is manufactured by laser cut process.

According to some embodiments, the ratio N (N=LI $D_{out}$) between the medical apparatus's 100 longitudinal length (L), as demonstrated in FIG. 1, and the diameter of the outer tubular wall ($D_{out}$) is smaller than a predetermined numeral selected from the group consisting of: 3, 2.5, 2, 1.5, 1, 0.5, 0.3 and any ratio within their range. According to a preferred embodiment, N is smaller than 1.5.

According to some embodiments, the first and second tubular walls are concentric. According to some embodiments, the medical apparatus is axisymmetric.

According to some embodiments, the material of the outer and inner tubular walls comprises at least one from the group consisting of: Nitinol, stainless steel, Titanium, Cobalt-Chromium alloy, Tantalum alloy, polymer (ePTFB, PU, etc.), Platinum alloy and any combination thereof.

According to some embodiments, the outer tubular wall is made of a first material and the inner tubular wall is made of a second material. According to some embodiments, the outer and inner tubular walls are made of the same material.

Figure 6A:
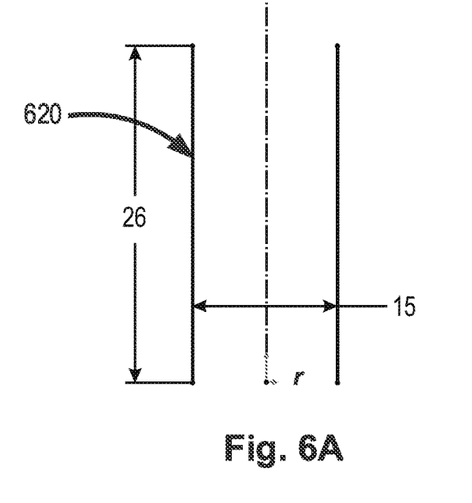
FIGS. 6A and 6B conceptually illustrate a non-limiting schematic example for a second tubular wall, according to some embodiments of the invention.
Figure 6B:
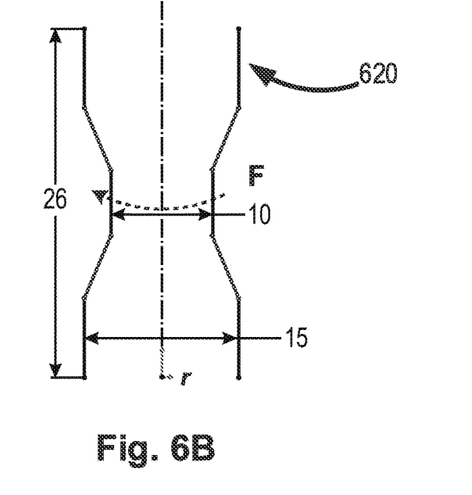

Reference is now made to FIGS. 6A and 6B, which demonstrate a non-limiting schematic example for a second tubular wall 620 before (FIG. 6A) and after (FIG. 6B) its constriction. In this non-limiting example, the overall initial longitudinal length of the second tubular wall is 26 mm and its initial diameter before its constriction is 15 mm. After a partial constriction of the second tubular wall, by applying a circumference constriction force (F) its minimal diameter is 10 mm, while its overall longitudinal length is kept 26 mm, such that the path length ($L_p$) of the second tubular wall has increased without an increase in its overall length (L).

Figure 6C:
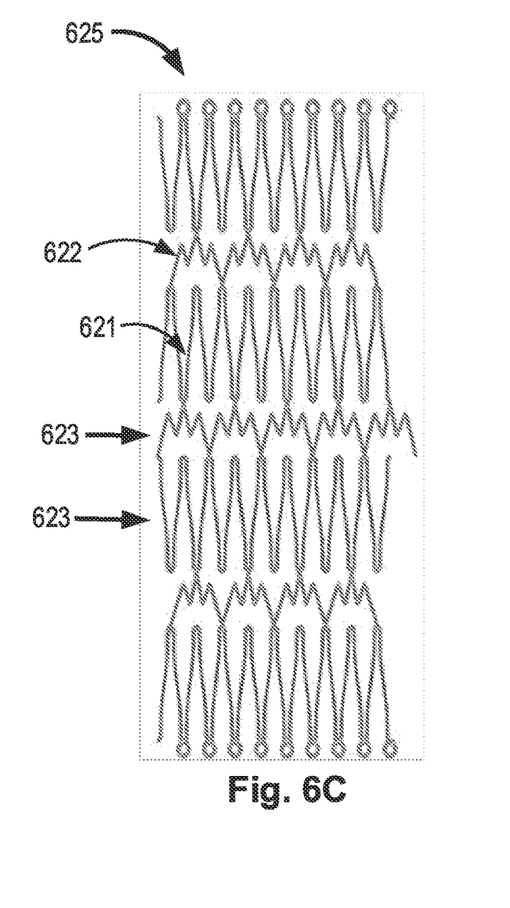
FIGS. 6C and 6D conceptually illustrate non-limiting flattened schematic examples for second tubular walls, according to some embodiments of the invention.
Figure 6D:
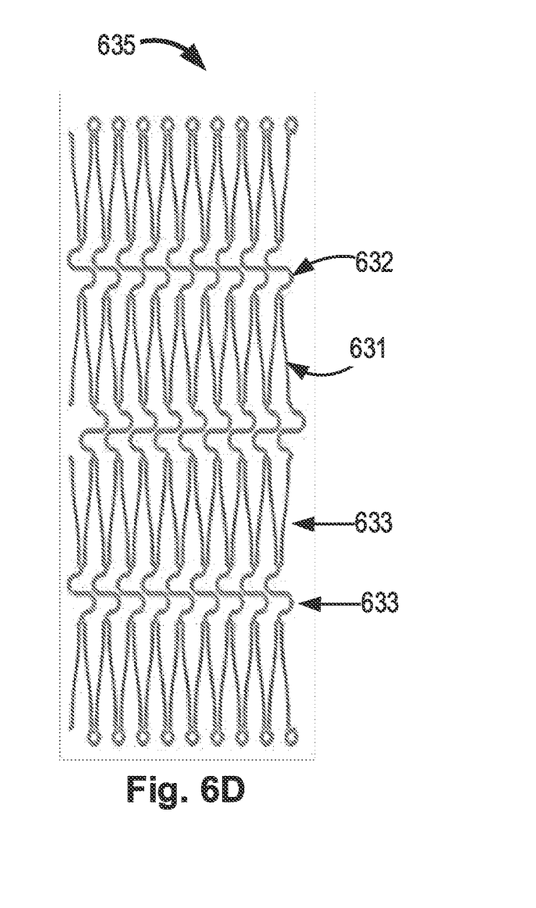

Reference is now made to FIGS. 6C and 6D, which schematically demonstrate two different non-limiting flattened schematic examples for second tubular walls, according to some embodiments of the invention. As shown, the second tubular wall 625,635 comprises, according to some embodiments, a plurality of strut elements 621,631 and a plurality of connecting elements 622,632. When a constriction force (F) is applied, at least some of the connecting elements are configured to be deformed and cause an increase in the distance between the strut elements rows/rings, therefore allowing a constriction of at least a part of the second tabular wall, with an increased path length, while maintaining its overall longitudinal length. The rows or rings-like configurations 623,633 are also demonstrated.

Reference is now made to FIG. 7, which conceptually depicts a stent like medical apparatus 700 having a first tubular wall and a second coated tubular wall. According to some embodiments of the invention the medical apparatus 700 comprises:
   a first tubular wall 710 (also noted as outer tubular wall); and
   a second tubular wall 720 (also noted as inner tubular wall), placed within the first tubular wall;
   wherein the first- and second-tubular walls are firmly connected at their proximal and distal edges 714,724, therefore restricted to have same overall longitudinal length; and wherein the second tubular wall is configured to be partially constricted 730 towards its inner radial axis, while maintaining its overall longitudinal length;

it is therefore that the combination of the first and second tubular walls forms a diametrical reducer.

FIG. 7 further demonstrates that at least a portion of the second tubular wall 720 is coated with a coating material 760, for example by an ePTFE, such that the flow through the vessel will be guided through the second tubular wall. FIG. 7 further demonstrates that in addition to the coating of the second tubular wall, the proximal and distal ends of the first tubular wall can be coated 770, according to some embodiments of the invention, to create a fluid seal with the coating of the second tubular wall.

Figure 8:
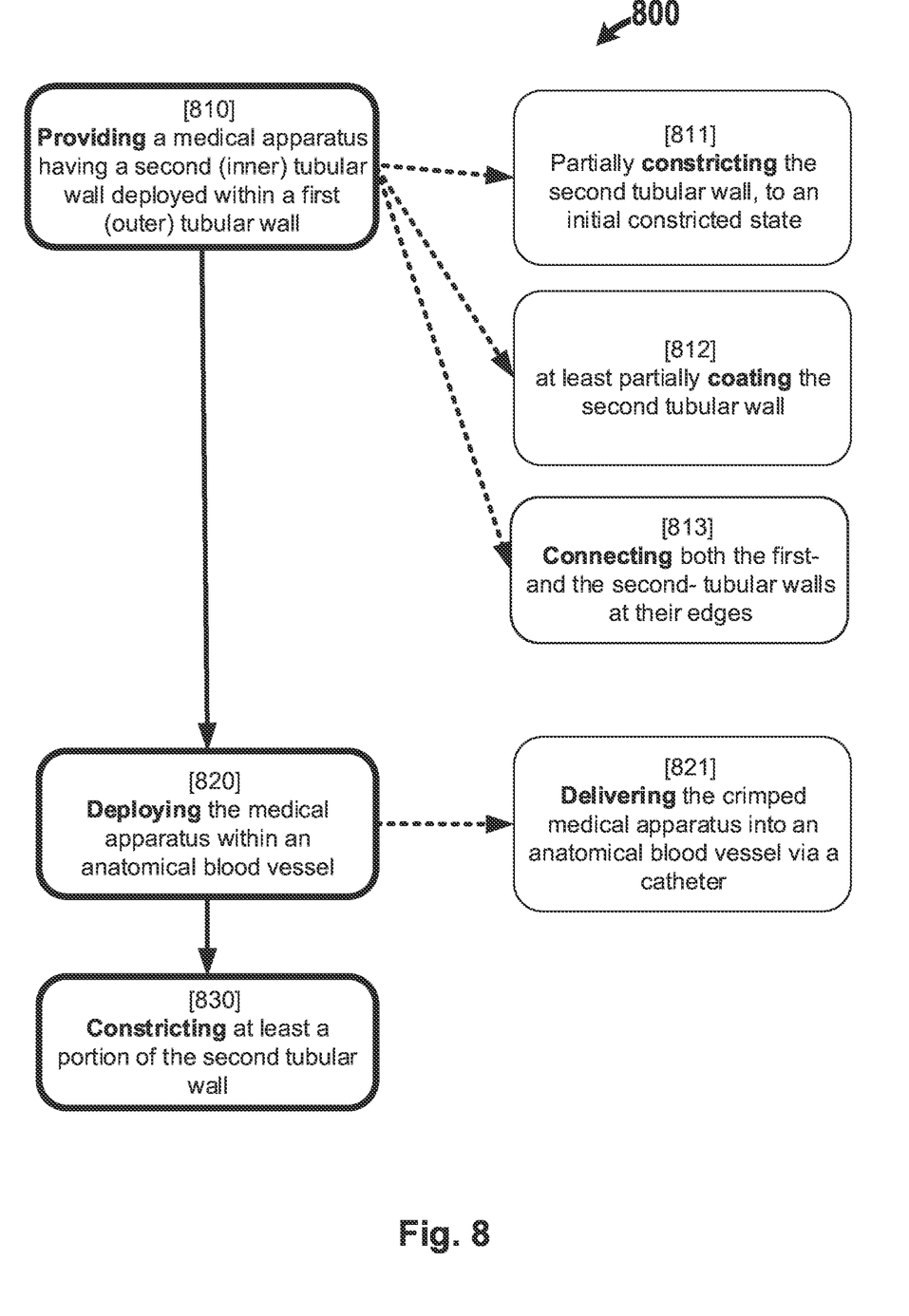
FIG. 8 conceptually demonstrates a method of use of an apparatus configured for a reduction of an effective diameter of an anatomic vessel, according to some embodiments of the invention.

Reference is now made to FIG. 8, which conceptually demonstrates a method of use of an apparatus configured for a reduction of an effective diameter of an anatomic vessel, according to any of the above-mentioned embodiments. The method 800 comprising:

providing 810 a medical apparatus having a second tubular wall placed within a first tubular wall;

deploying 820 the medical apparatus within an anatomical blood vessel; and constricting 830 at least a portion of the second tubular wall, thereby providing the second tubular wall with a radial neck section, while maintaining its overall longitudinal length.

According to some embodiments, the step of providing further comprises partially constricting 811 the second tubular wall to an initial constricted state, which may be further constricted. According to some embodiments, the initial constriction is provided via a heating process; for example, by heat treatment of the Nitinol of the second tubular wall to maintain a specific shape; for example, to have a shape of an hourglass.

According to some embodiments, the step of providing further comprises at least partially coating 812 the second tubular wall.

According to some embodiments, the step of providing further comprises connecting 813 both the first- and the second-tubular walls at their edges, thereby restricting the first- and the second-tubular walls to have the same overall longitudinal length.

According to some embodiments, the step of deploying comprises delivering 821 the medical apparatus into an anatomical blood vessel via a catheter, wherein the medical apparatus is provided in a crimped configuration, which is configured to expand back, once deployed out of the delivering catheter.

According to some embodiments, a therapeutic result for the use of a medical apparatus as mentioned above, for patients with LV heart failure, can be at least one of the group consisting of:

an increase in the left ventricle ejection fraction (LVEF);

a decrease in the left ventricle end diastolic pressure (LVEDP);

improvement in the clinical symptoms of heart failure; and any combination thereof.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A medical apparatus for deployment within an anatomical blood vessel comprising:
   a first tubular wall; and
   a second tubular wall, placed within the first tubular wall, the second tubular wall comprising a plurality of sections, one or more of said plurality of sections comprising struts,
   and
   wherein the second tubular wall is configured to be partially constricted towards its inner radial axis, while maintaining its overall longitudinal length by deformation of one or more of said struts, under a constriction force said first and second tubular walls forming a diametrical reducer.

2. The medical apparatus of claim 1, wherein said first and second tubular walls are firmly connected at their edges, therefore restricted to have the same overall longitudinal length.

3. The medical apparatus of claim 2, wherein at least one of the first and the second tubular walls comprises binding elements at its edges, configured for the connection of the first and the second tubular walls one to another.

4. The medical apparatus of claim 1, wherein the plurality of sections comprise strut elements and connecting elements; and wherein struts of the connecting elements are configured to be deformed, when a constriction force is applied.

5. The medical apparatus of claim 1, wherein at least some of the sections are arranged in one or both of:
   rows; and
   a ring-like configuration.

6. The medical apparatus of claim 1, wherein the sections' motion comprises at least one of: deformation, translation, rotation, twist, contraction, conversion and collapse.

7. The medical apparatus of claim 1, further comprising a constricting element configured to constrict a circumference of a portion of the second tubular wall.

8. The medical apparatus of claim 1, wherein the constriction provides the second tubular wall with a radial neck section, configured for reduction of the effective diameter of the anatomical blood vessel, and wherein at least a portion of the second tubular wall is coated with a coating material.

9. The medical apparatus of claim 1, wherein the first and second tubular walls are concentric.

10. The medical apparatus of claim 1, wherein material of the first and second tubular walls comprises at least one of the group consisting of: Nitinol, stainless steel, Titanium, Cobalt-Chromium alloy, Tantalum alloy, polymer, Platinum alloy and any combination thereof.

11. The medical apparatus of claim 1, wherein the first tubular wall is made of a first material and the second tubular wall is made of a second material.

12. The medical apparatus of claim 1, wherein at least one of the first and second tubular walls are manufactured by a laser cut process.

13. The medical apparatus of claim 1, wherein the ratio between the medical apparatus's longitudinal length and diameter of the first tubular wall is smaller than three (3).

14. The medical apparatus of claim 1, wherein the medical apparatus is reversibly collapsible and configured to be delivered into the anatomic vessel via a catheter.

15. A method of use of an apparatus configured for reduction of effective diameter of an anatomic vessel, the method comprising:
   providing a medical apparatus having a second tubular wall placed within a first tubular wall, wherein the second tubular wall includes a plurality of sections one or more of said plurality of sections comprising struts;

wherein the second tubular wall is configured to be partially constricted towards its inner radial axis, while maintaining its overall longitudinal length by deformation of one or more of said struts, under a constriction force;

deploying the medical apparatus within an anatomical blood vessel; and constricting at least a portion of the second tubular wall with said constriction force, to initiate said deformation of said one or more of said struts, thereby providing the second tubular wall with a radial neck section, while maintaining its overall longitudinal length, said first and said second tubular walls forming a diametrical reducer.

16. The method of claim 15, wherein the constricting is provided, while the medical apparatus is within the anatomic vessel.

17. The method of claim 15, wherein the step of providing comprises partially constricting the second tubular wall.

18. The method of claim 15, wherein the step of providing comprises at least partially coating the second tubular wall.

19. The method of claim 15, wherein the step of providing comprises connecting both the first- and the second-tubular walls at their edges, thereby restricting the first- and the second-tubular walls to have the same overall longitudinal length.

20. The method of claim 15, wherein the step of deploying comprises delivering the medical apparatus into an anatomical blood vessel via a catheter.

21. A medical apparatus for deployment within an anatomical blood vessel comprising:

a first tubular wall; and a second tubular wall, placed within the first tubular wall, the second tubular wall comprising a plurality of sections comprising: strut element sections and connecting element sections, and having an inner radial axis and an overall longitudinal length;

wherein the first and second tubular walls are connected; and wherein the second tubular wall is configured to be:
partially constricted towards said inner radial axis, while maintaining said overall longitudinal length;
by deformation of said connecting element sections which moves at least some of the strut element sections one relative to another;

wherein said medical apparatus including said first and second tubular walls forms a diametrical reducer.

22. The medical apparatus of claim 21, wherein said deformation rotates one or more of said plurality of sections with respect to each other about a longitudinal axis of said second tubular structure.

23. The medical apparatus of claim 22, wherein said strut element sections are connected by said connecting element sections, wherein said deformation rotates one or more of said strut element sections with respect to another one or more of said strut sections.

24. The medical apparatus of claim 23, wherein said second tubular wall is connected at its edges to said first tubular walls.

* * * * *